United States Patent [19]
Ekechukwu

[11] Patent Number: 5,583,051
[45] Date of Patent: Dec. 10, 1996

[54] USE OF A FIBER OPTIC PROBE FOR ORGANIC SPECIES DETERMINATION

[75] Inventor: Amy A. Ekechukwu, Augusta, Ga.

[73] Assignee: The United States of America as represented by the Department of Energy, Washington, D.C.

[21] Appl. No.: 380,921

[22] Filed: Jan. 31, 1995

Related U.S. Application Data

[63] Continuation of Ser. No. 12,865, Feb. 3, 1993, abandoned.

[51] Int. Cl.⁶ ................................................. G01N 21/63
[52] U.S. Cl. .................... 436/169; 436/171; 422/82.06
[58] Field of Search ........................... 422/56, 82.06, 422/82.07, 82.08, 82.09, 82.11; 436/139–142, 143, 145, 146, 169, 171; 385/12

[56] References Cited

U.S. PATENT DOCUMENTS

| | | | |
|---|---|---|---|
| 4,069,016 | 1/1978 | Wu | 436/97 |
| 4,200,110 | 4/1980 | Peterson et al. | 422/58 X |
| 4,523,092 | 6/1985 | Nelson | 250/227 |
| 4,560,248 | 12/1985 | Cramp et al. | 350/96.34 |
| 4,752,115 | 6/1988 | Murray, Jr. et al. | 350/96.29 |
| 4,842,783 | 6/1989 | Blaylock | 264/1.4 |
| 4,886,338 | 12/1989 | Yafuso et al. | 350/96.29 |
| 4,892,383 | 1/1990 | Klainer et al. | 385/12 |
| 4,925,268 | 5/1990 | Iyer et al. | 350/96.29 |
| 4,999,306 | 3/1991 | Yafuso et al. | 436/68 |
| 5,045,282 | 9/1991 | Kritzman et al. | 422/56 |
| 5,096,671 | 3/1992 | Kane et al. | 422/82.07 |
| 5,114,676 | 5/1992 | Leiner et al. | 422/82.06 |
| 5,116,759 | 5/1992 | Klainer et al. | 435/288 |
| 5,119,463 | 6/1992 | Vurek et al. | 385/129 |

Primary Examiner—Jeffrey R. Snay
Attorney, Agent, or Firm—Harold Dixon; William R. Moser; Paul A. Gottlieb

[57] ABSTRACT

A fiber optic probe for remotely detecting the presence and concentration of organic species in aqueous solutions. The probe includes a cylindrical housing with an organic species indicator, preferably diaminonaphthyl sulfonic acid adsorbed in a silica gel (DANS-modified gel), contained in the probe's distal end. The probe admits aqueous solutions to the probe interior for mixing within the DANS-modified gel. An optical fiber transmits light through the DANS-modified gel while the indicator reacts with organic species present in the solution, thereby shifting the location of the fluorescent peak. The altered light is reflected to a receiving fiber that carries the light to a spectrophotometer or other analysis device.

13 Claims, 1 Drawing Sheet

U.S. Patent        Dec. 10, 1996        5,583,051
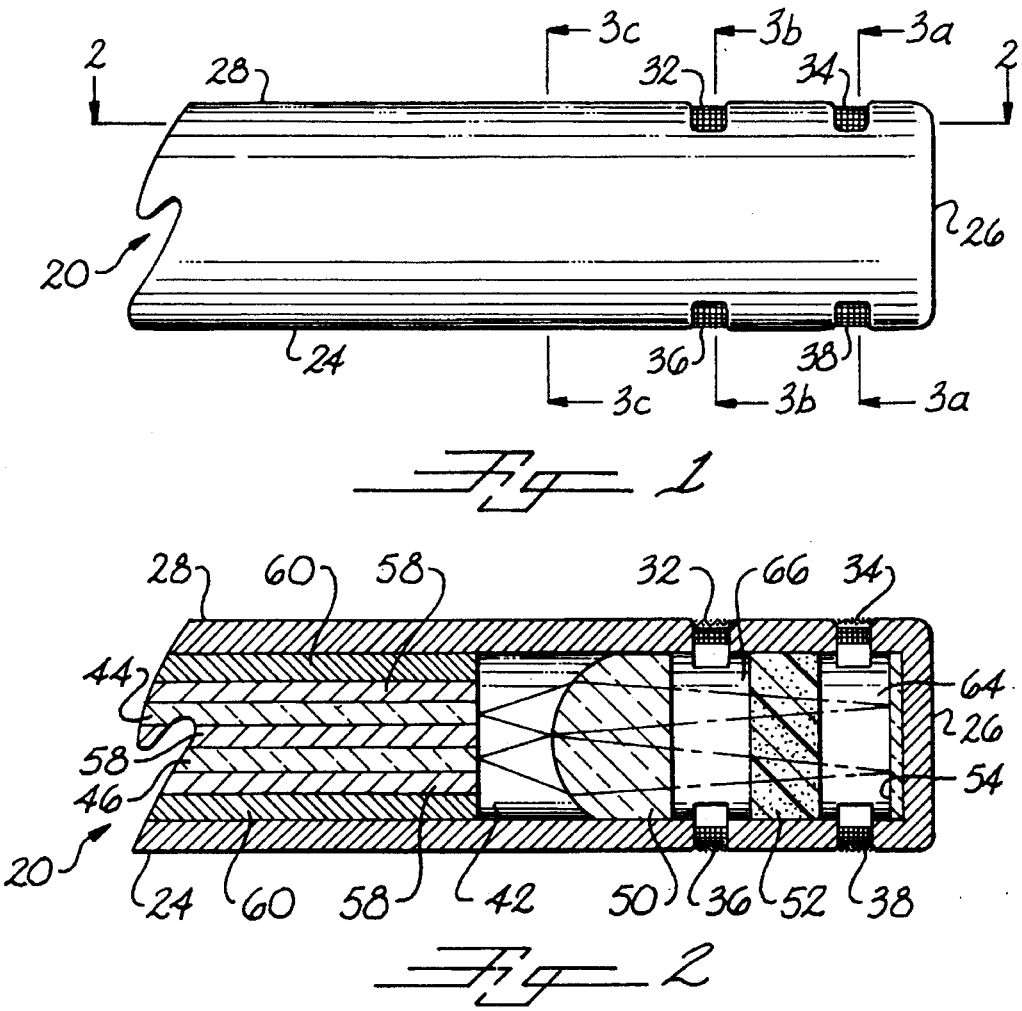
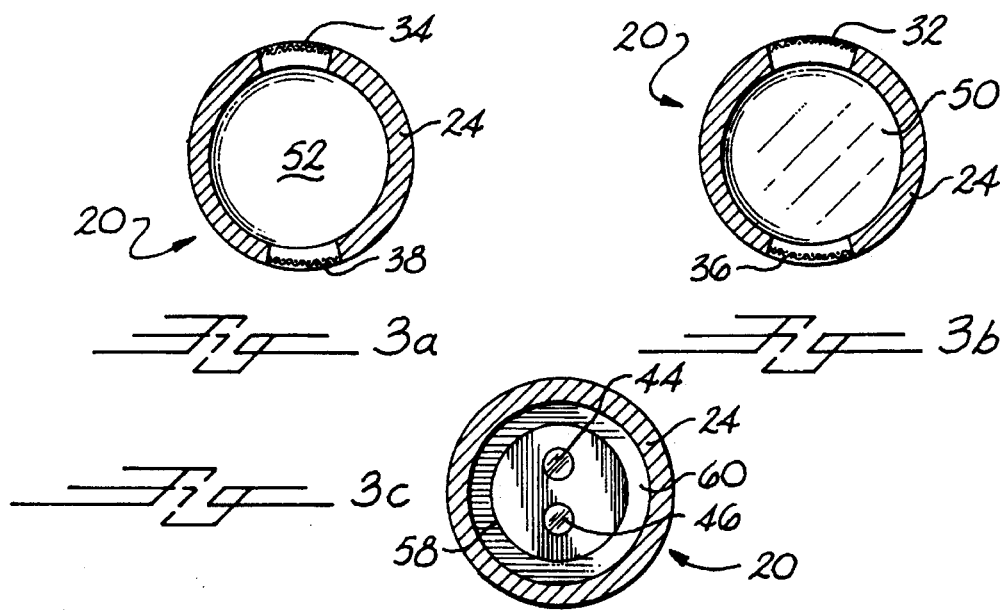

USE OF A FIBER OPTIC PROBE FOR ORGANIC SPECIES DETERMINATION

The United States Government has rights in this invention pursuant to Contract No. DE-AC09-89SR18035 between the U.S. Department of Energy and Westinghouse Savannah River Company.

This is a continuation of application Ser. No. 08/012,865 filed Feb. 3, 1993, now abandoned.

BACKGROUND OF THE INVENTION

1. Field of the Invention

The present invention relates to detection of organic compounds. More particularly, the present invention relates to fiber optic probes for detection and measurement of organic wastes in groundwater.

2. Discussion of Background

Fiber optic sensing devices for detecting the existence and extent of chemicals or changes in chemical or physical parameters are well known. Such devices, whether they are probes for continuous remote operation or sensors used for laboratory analysis techniques, typically contain some type of indicator responsive to the presence of an analyte in fluids or gases. The indicator, upon mixing with the chemical compound, may react with it or be changed in some other way, to indicate the presence and concentration of the compound. Indicators are known for detecting such analytes as oxygen, carbon dioxide, hydrogen (i.e. pH), certain metal ions, and biological fluids such as glucose and ammonia.

When used in conjunction with fiber optic devices, the optical characteristics of these indicators in response to the presence of a corresponding analyte offer a range of possibilities for detection and analysis. For example, analytes may affect the fluorescent emission, reflection, or absorption spectrum of light passing through the indicator in the presence of that particular analyte.

Fiber optic detecting systems using spectrometric absorption analysis techniques typically include a light source, a sample cell containing the fluid of interest, an indicator and a detector, such as a spectrophotometer. Light is passed through the sample cell and received by the spectrophotometer, which measures the absorption spectrum of the received light. Devices for remote operation are typically in the form of probes using fiber optics to transmit and receive light signals.

Numerous methods exist for securing the indicator within these probes. Typically, polymer matrices positioned in the probes are used to carry the indicators through absorption, adsorption, or other methods.

Specific examples of sensing devices include U.S. Pat. No. 4,842,783, issued to Blaylock, and U.S. Pat. No. 5,119,463, issued to Vurek et al. Blaylock discloses a fiber optic sensor for detecting certain metal ions and pH, among other analytes. The sensor uses an indicator dye absorbed into a polymeric gel contained within the sensor. Similarly, Vurek et al disclose a fiber optic probe for determining the presence of $O_2$, $CO_2$, and pH using analyte indicators disposed on polymer matrices.

In U.S. Pat. No. 5,096,671, Kane et al disclose a fiber optic sensor using a detection indicator dispersed within a hydrogel matrix. Also, Yafuso et al, in U.S. Pat. Nos. 4,999,306 and 4,886,338, disclose a fiber optic sensor for detecting the concentration of an ionic component in a medium, using a sensing material chemically bonded to an ionic matrix contained within the sensor. In one particular embodiment, sulfonic acid absorbed within a hydrogel is used as a pH indicator for the fiber optic sensor.

Still, despite the abundance of fiber optic probes using well known indicators, it is believed that certain monitoring and detection needs have yet to be met adequately. For instance, the identification of trace amounts of organic compounds in aqueous solutions has been difficult to achieve due to high water content in the solutions interfering with the detection response. The detection of low levels of organic species, particularly in aqueous solutions, is a growing health and safety concern for our environment, thus, there is an immediate need for detectors of this kind.

It is believed that no effective sensor or remote probe exists for detecting small amounts of organic species in aqueous solutions.

SUMMARY OF THE INVENTION

According to its major aspects and broadly stated, the present invention is a fiber optic probe for detecting the presence and concentrations of organic compounds in aqueous solutions. The probe is a hollow housing with an organic species indicator, preferably 5-dimethylamino-1-naphthalene sulfonate salt (DANS), adsorbed onto a substrate and contained in the probe's interior. The substrate is preferably a silica gel. The probe admits fluids through openings in the housing that mix with the DANS-modified gel. An optical fiber shines the light through the DANS-modified gel where the indicator has mixed with organic species present in the solution and altered the absorption spectrum from a first spectrum to a second spectrum. The first indicates no organic compound present, the second indicates the presence of an organic compound with the spectrum shifting continuously from the first to the second spectrum. The altered spectrum is reflected by a mirror to a receiving optic fiber that carries the light to the spectrophotometer.

A major feature of the present invention is the use of 5-dimethylamino-1-naphthalene sulfonate salt (DANS) acid as an analyte indicator for organic species. When mixed with aqueous organic solutions, 5-dimethylamino-1-naphthalene sulfonate salt (DANS) absorbs light passing through the sample solution to varying degrees depending on the concentration of the organic species present in the solution.

Another feature of the present invention is the combination of 5-dimethylamino-1-naphthalene sulfonate salt (DANS) and a silica gel substrate. The porous gel can hold a quantity of DANS acid and take up a sample of the solution in such a way the two can mix sufficiently for the spectral shift to occur.

Still another feature of the present invention is the arrangement of the probe components. The transmitting and receiving optic fibers are in parallel and adjacent with a mirror positioned to reflect light from the transmitting to the receiving fibers once it has crossed the substrate with the solution and DANS acid in it. A lens may be added to focus the light. The advantage of this feature is that the probe may be compact and easier to implant in the soil, for example, since both optic fibers enter the probe from the same end.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a side view of a fiber optic sensing probe according to a preferred embodiment of the present invention;

FIG. 2 is a side cross-sectional view of the probe taken along the lines 2—2 of FIG. 1;

FIG. 3a is a partial cross-sectional view of the probe taken along lines 3a—3a of FIG. 1;

FIG. 3b is a partial cross-sectional view of the probe taken along lines 3b—3b of FIG. 1; and FIG. 3c is a partial cross-sectional view of the probe taken along lines 3c—3c of FIG. 1.

DETAILED DESCRIPTION OF A PREFERRED EMBODIMENT

In the following description similar components are referred to by the same reference numeral in order to simplify the understanding of the sequential aspect of the drawings.

Referring now to FIG. 1, the fiber optic probe 20 in its preferred embodiment is a slender, hollow, cylindrical housing 24 having a distal end 26 and a proximal end (shown generally as 28). Housing 24, preferably made of a durable, non-corrosive material such as stainless steel, but can be made of any material suitable for carrying the internal components (shown and discussed below) needed for operation of probe 20.

A plurality of openings formed in distal end 26 of housing 24 allows the aqueous solution to enter and exit the interior of housing 24. The opening are covered by a plurality of screens 32, 34, 36, and 38 in order to prevent foreign matter contained in the aqueous solution from entering housing 24, possibly lodging in housing 24 and decreasing operational effectiveness. Screens 32, 34, 36, and 38 are preferably made of a mesh material sufficient to allow the aqueous solution easy access into and out of the interior of housing 24, yet sturdy enough and of sufficiently fine mesh to prevent the entry of foreign matter such as dirt.

The interior of housing 24, as shown in FIG. 2, comprises a cavity 42 containing a transmitting fiber 44, a receiving fiber 46, a focusing lens 50, a substrate 52, and a reflector 54. Transmitting fiber 44 is preferably an optical fiber running axially along the interior of housing 24. Similarly, receiving fiber 46 is preferably an optical fiber adjacent to and parallel with transmitting fiber 44, and also running axially along the interior of housing 24.

The orientation of transmitting fiber 44 and receiving fiber 46 with respect to each other is maintained by an aligning piece 58 (shown also in FIG. 3c) that completely surrounds transmitting fiber 44 and receiving fiber 46. Aligning piece 58 is preferably made of rubber or some other material suitable for maintaining the spacing between transmitting fiber 44 and receiving fiber 46 along the interior of housing 24.

An additional spacer 60 (shown also in FIG. 3c) between housing 24 and aligning piece 58 maintains the separation of transmitting fiber 44 and receiving fiber 46 with respect to housing 24. Spacer 60 may be made of rubber or other suitable material for properly maintaining separation. Alternatively, spacer 60 can be simply an extension or extra thick segment of housing 24.

Spaced apart from transmitting fiber 44 and receiving fiber 46 within cavity 42 is a lens 50 (also shown in FIG. 3b). Lens 50 is preferably made of glass and dimensioned to fit snugly within the radial spacing of cavity 42. Lens 50 is positioned in cavity 42 to focus and direct light from transmitting fiber 44 to substrate 52, that is, light being transmitted toward distal end 26. The position of lens 50 in cavity 42 also allows light traveling away from distal end 26 to be directed toward receiving fiber 46.

Further along in cavity 42, toward distal end 26, is a substrate 52 (also shown in FIG. 3a) positioned axially distal to lens 50. Substrate 52 is preferably a silica gel or other polymeric substrate suitable for adsorbing an analyte indicator, preferably 5-dimethylamino-1-naphthalene sulfonate salt (DANS). Substrate 52 should also be of a material that allows aqueous solutions to pass. Substrate 52 is positioned along cavity 42 so that light from lens 50 is directed through substrate 52 to reflector 54, and light reflected off of reflector 54 passes through substrate 52 to lens 50.

Reflector 54 occupies the most distal portion of cavity 42 within housing 24. Reflector 54 is preferably glass or any other material suitable for reflecting light away from distal end 26.

In FIG. 3a, a cross-sectional view of housing 24 taken at the most distal set of openings, is shown. As previously identified, screens 34 and 38 cover two of preferably four openings formed in housing 24. Screens 34 and 38 each cover an arcuate opening of approximately 45° formed along housing 24. While the size of each opening may vary, they should be of the size that allows adequate flow of the aqueous solution into a cavity area 64 between substrate 52 and reflector 54.

Similarly, in FIG. 3b, a cross-sectional view of housing 24 taken at the second set of openings, is shown. Screens 32 and 36 each cover an arcuate opening of approximately 45° formed along housing 24. Similar to the openings covered by screens 34 and 38, the openings covered by screens 32 and 36 should be of the size that allow adequate flow of the aqueous solution into a cavity area 66 between lens 50 and substrate 52.

Referring now to FIG. 3c, aligning piece 58 is shown surrounding transmitting fiber 44 and receiving fiber 46, thereby maintaining their adjacent and parallel spatial relationship. By adjacent, it is meant that the two fibers are "side-by-side" and close but not necessarily touching. Also, spacer 60 is shown surrounding aligning piece 58, thereby maintaining the separation between aligning piece 58 and housing 24.

In use, distal end 26 of housing 24 is placed in an aqueous solution of interest so that the aqueous solution can enter cavity 42 generally between lens 50 and reflector 54. As previously described, substrate 52 allows the aqueous solution to pass, therefore, the solution entering the opening covered by screen 34 can exit cavity 42 through any of the openings covered by screens 32, 36, and 38. It is also possible for solution entering the opening covered by screen 34 to exit the same opening, depending on the flow direction of the aqueous solution.

Once distal end 26 is placed in an appropriate sample environment, the aqueous solution entering cavity 42 through the openings mixes and interacts with the organic species indicator adsorbed on substrate 52, which is preferably 5-dimethylamino-1-naphthalene sulfonate salt (DANS). A light source (not shown) attached to transmitting fiber 44 at its proximal end (not shown) allows light to be carried down transmitting fiber 44 in the direction from proximal end 28 to distal end 26.

Upon emergence from transmitting fiber 44, the light passes to lens 50, which focuses and directs the light through substrate 52. Since the indicator adsorbed in substrate 52 is of the kind that absorbs light or shifts the location of the fluorescent peak in the presence of organic species, the light passing through substrate 52 is altered depending on the concentration of organic species in the aqueous solution near substrate 52.

The light passing through substrate 52 travels to reflector 54, which reflects the light away from distal end 26 and back through substrate 52. Light traveling back through substrate 52 then passes to lens 50, which directs it generally to receiving fiber 46. Receiving fiber 46 collects the altered light and carries it back to a spectrophotometer (not shown) or other analysis device, which is preferably connected to the proximal end (not shown) of receiving fiber 46.

It will be apparent to those skilled in the art that many changes and substitutions can be made to the preferred embodiment herein described without departing from the spirit and scope of the present invention as defined by the appended claims.

What is claimed is:

1. A method for the detection of organic species in a solution, said method comprising the steps of:

directing light through an indicator;

measuring a first absorption spectrum of said indicator;

contacting said solution with said indicator to form a mixture;

directing light through said mixture;

measuring a second absorption spectrum of said mixture;

comparing said fast absorption spectrum and said second absorption spectrum to determine a difference between said first and said second absorption specta; and analyzing said difference to determine the presence of organics in said solution wherein said indicator is a 5-dimethylamino-1-naphthalene sulfonate salt.

2. A method as recited in claim 1, further comprising:

determining the magnitude of said difference, said magnitude being related to said difference.

3. A method as recited in claim 1, wherein said indicator is fixed in a housing, and wherein said contacting step takes place in said housing.

4. A method as recited in claim 1, wherein said indicator is fixed in a housing having a plurality of openings; and said method further comprises filtering foreign matter from said solution by passing said solution through said plurality of openings before said contacting step.

5. A method as recited in claim 1, wherein said indicator is fixed in a housing having a plurality of openings;

said method further comprises filtering foreign matter from said solution by passing said solution through said plurality of openings before said contacting step; and wherein said contacting step takes place in said housing.

6. A method as recited in claim 1, further comprising the step of adsorbing said indicator on a substrate.

7. A method as recited in claim 1, further comprising the step of adsorbing said indicator on a modified silica gel substrate.

8. A method as recited in claim 1, wherein said indicator is a 5-dimethylamino-1-naphthalene sulfonate salt, said method further comprising absorbing said 5-dimethylamino-1-naphthalene sulfonate salt on a substrate.

9. A method as recited in claim 1, wherein said indicator is a 5-dimethylamino-1-naphthalene sulfonate salt, said method further comprising absorbing a 5-dimethylamino-1-naphthalene sulfonate salt on a modified silica gel substrate.

10. A method as recited in claim 1, wherein in each of said directing steps said light is directed through a optical focusing device.

11. A method as recited in claim 1, wherein in each of said directing steps said light is reflected to a means for measuring said first and said second absorption specta.

12. A method as recited in claim 1, wherein in each of said directing steps said light is directed through an optical focusing device and reflected to a means for measuring said first and said second absorption spectra.

13. A method for the determination of organic species in a solution, said method comprising the steps of:

adsorbing an indicator on a substrate, wherein said indicator adsorbed on said substrate is fixed in a housing having a plurality of openings;

directing light through said indicator;

measuring a first absorption spectrum of said indicator;

filtering foreign matter from said solution by passing said solution through said plurality of openings;

contacting said solution with said indicator in said housing to form a mixture;

directing light through said mixture;

measuring a second absorption spectrum of said mixture;

comparing said first absorption spectrum and said second absorption spectrum to determine a difference between said first and said second absorption spectra; and analyzing said difference to determine the presence of organics in said solution wherein said indicator is a 5-dimethylamino-1-naphthalene sulfonate salt.

* * * * *